United States Patent [19]

Anello et al.

[11] 4,110,408
[45] Aug. 29, 1978

[54] PREPARATION OF 1-CHLORO-2-TRIFLUOROMETHYL-3,3,3-TRIFLUOROPROPENE FROM ISOBUTYLENE

[75] Inventors: Louis G. Anello, Hamburg; Richard F. Sweeney, Elma, both of N.Y.

[73] Assignee: Allied Chemical Corporation, Morris Township, Morris County, N.J.

[21] Appl. No.: 858,131

[22] Filed: Dec. 7, 1977

Related U.S. Application Data

[62] Division of Ser. No. 753,065, Dec. 21, 1976.

[51] Int. Cl.$^2$ .............................................. C07C 17/20
[52] U.S. Cl. .............................. 260/653.4; 260/653.5; 260/653.7; 260/654 H
[58] Field of Search ............... 260/653.4, 653.5, 653.7, 260/654 H

[56] References Cited

U.S. PATENT DOCUMENTS

| 2,889,379 | 6/1959 | Ruh et al. | 260/653.4 |
| 2,996,555 | 8/1961 | Rausch | 260/653.4 |
| 3,183,276 | 5/1965 | Vecchio | 260/653.4 |
| 3,787,331 | 1/1974 | Groppelli et al. | 260/653.7 |

FOREIGN PATENT DOCUMENTS

| 921,254 | 3/1963 | United Kingdom | 260/653.4 |
| 1,087,873 | 10/1967 | United Kingdom | 260/653.4 |

*Primary Examiner*—C. Davis

[57] ABSTRACT

Isobutylene is catalytically converted to 1-chloro-2-trifluoromethyl-3,3,3-trifluoropropene [$(CF_3)_2C = CHCl$] in a chlorofluorination reaction zone by passing a mixture of anhydrous hydrogen fluoride, chlorine and the isobutylene over a chromium oxide or metal fluoride chlorofluorination catalyst. Alternatively, the isobutylene feed is first prechlorinated, and the mixture of prechlorination fed for conversion to the desired $(CF_3)_2C = CHCl$, to a downstream fluorination reactor charged with the chlorofluorination catalyst.

17 Claims, No Drawings

PREPARATION OF 1-CHLORO-2-TRIFLUOROMETHYL-3,3,3-TRIFLUOROPROPENE FROM ISOBUTYLENE

This is division of application Ser. No. 753,065 filed Dec. 21, 1976.

BACKGROUND OF THE INVENTION

1. Field of the Invention

The present invention relates to a process for the preparation of 1-chloro-2-trifluoromethyl-3,3,3-trifluoropropene [$(CF_3)_2C = CHCl$] from isobutylene, and, more especially, relates to the preparation of 1-chloro-2-trifluoromethyl-3,3,3-trifluoropropene by the catalytic chlorofluorination of isobutylene.

2. Description of the Prior Art:

1-Chloro-2-trifluoromethyl-3,3,3-trifluoropropene is a known compound. This olefin is of value as an intermediate in the preparation of hexafluoroisobutylene. Hexafluoroisobutylene, i.e., 3,3,3-trifluoro-2-trifluoromethyl-1-propene, is a valuable commercial monomer used in the production of a number of polymeric materials. Among such polymers is the copolymer with vinylidene fluoride, the preparation of which is described in U.S. Pat. No. 3,706,723 to Cnandrasekeran et al. Hexafluoroisobutylene is presently advantageously prepared from hexafluoroacetone and ketene. See U.S. Pat. No. 3,894,097 to Vanderkooi, Jr., et al. The high costs and limited availability of hexafluoroacetone nevertheless militate against the use of this route for manufacturing commercial quantities of hexafluoroisobutylene. Alternate routes to the preparation of hexafluoroisobutylene are, for example, disclosed or noted in the aforesaid '097 Vanderkooi, Jr. et al patent, as well as in the U.S. Pat. No. 3,655,786 to Gilbert et al.

The known 1-chloro-2-trifluoromethyl-3,3,3-trifluoropropene has itself been prepared by the chlorofluorination of isobutylene in the presence of elemental carbon. Compare British Patent Specification No. 1,087,873. Isobutylene has also been non-catalytically chlorofluorinated in an empty tube, as per Canadian Pat. No. 942,323 and U.S. Pat. No. 3,436,430 to Hall. Nonetheless, the procedures disclosed in these patents are unsatisfactory because the yields of product 1-chloro-2-trifluoromethyl-3,3,3-trifluoropropene are low and, for that matter, conducting the procedures outlined at examples 1 and 2 of the '873 British patent even gives rise to concomitant, massive breakdown to halomethanes.

SUMMARY OF THE INVENTION

It is, therefore, a primary object of the invention to provide a process for the preparation of 1-chloro-2-trifluoromethyl-3,3,3-trifluoropropene from isobutylene which avoids the difficulties and shortcomings of the prior art processes.

Another object of the invention is to provide a process for the preparation of 1-chloro-2-trifluoromethyl-3,3,3-trifluoropropene from isobutylene, wherein the $(CF_3)_2C = CHCl$ is produced in high conversion and in continuous manner.

Yet another object of the invention is to provide a process for the catalytic chlorofluorination of isobutylene to $(CF_3)_2C = CHCl$ without either concomitant breakdown to halomethanes or carbonization.

These and other objects, features and advantages of the invention will become more apparent from the description which follows.

In accordance with a first embodiment of this invention, isobutylene is catalytically chlorofluorinated to $(CF_3)_2C = CHCl$ in a single reaction zone by passing a mixture of anhydrous hydrogen fluoride [HF], chlorine and the isobutylene over a chromium oxide or metal fluoride chlorofluorination catalyst.

According to a second embodiment of the invention, the isobutylene feed is first prechlorinated, either in a single step or a multiplicity of steps, and the mixture of prechlorination fed for conversion to the desired $(CF_3)_2C = CHCl$, either directly or indirectly, to a downstream fluorination reactor charged with the chromium oxide or metal fluoride chlorofluorination catalyst.

DETAILED DESCRIPTION OF THE INVENTION

In one embodiment of the process according to this invention, anhydrous hydrogen fluoride, chlorine, and isobutylene are charged to a reactor and are passed over certain metal chlorofluorination catalysts, i.e., chromium oxide or metal fluoride chlorofluorination catalysts. The gases exiting from the reactor are then conveyed through suitable product recovery system, e.g., desirably passed through a water scrubber, a caustic scrubber, a drying tower, and finally condensed in a dry ice/acetone cooled trap. A portion of the product mixture is found in the water scrubber, with the remainder being in the dry ice/acetone cooled trap. The organic product in the water trap is next phase separated, dried, and combined with the contents of the cold trap, and the desired $(CF_3)_2C = CHCl$ product separated by distillation.

Although the chlorofluorination reactions can be carried out in a single reactor, it is generally preferred to prechlorinate the isobutylene and to pass a mixture of chloroisobutanes and chloro-isobutenes into the fluorination reactor according to a second embodiment of the invention. Prechlorination decreases the amount of breakdown products. The prechlorination can be carried out in a single step or in a plurality of steps. The product of the chlorination step can be passed directly into the fluorination reactor or collected and fed into the fluorination reactor at a later point in time. It is most important that an average of between four and five chlorine atoms be present in the organic molecule fed to the fluorination reactor. A particularly preferred method of achieving this degree of chlorination comprises the use of two chlorination stages. In the first stage, the isobutylene and chlorine are advantageously mixed in a tubular reactor at room temperature and then passed into a second heated tubular reactor. The reaction in the first reactor produces an exotherm, but no external heating is applied. The contact time in the first reactor desirably ranges from between about 0.01 to 1 second. A contact time of about 0.2 seconds is preferred. The second reactor is heated to about 300° to 400° C. A preferred temperature is about 375° C. The contact time in the second reactor usually varies from between about 1 and 50 seconds, with the preferred contact time being in the range of between about 5 and 20 seconds. The chlorine/isobutylene mole ratio desirably varies between about 2:1 to 12:1, with 4:1 to 6:1 ratio being the preferred. An inert gas stream consisting of nitrogen or helium is generally mixed with the chlorine feed to sweep the reactants through the system. The products of the chlorination reaction may be passed as vapor directly into the downstream fluorination reactor, or condensed and separated from HCl and insufficiently halogenated products by distillation. This collected chlorinated organic may then be revaporized and passed into the fluorination reactor at any later point in time. It is critical that an average chlorine content of at least 4 chlorine atoms per molecule of organic be achieved.

The chlorination reactors are preferably tubular, constructed of material resistant to both chlorine and HCl, with Inconel being particularly preferred.

The chlorination of the isobutylene can be conducted either in vapor or in liquid phase. The isobutylene and the chlorine, for example, can be passed into and dissolved in a suitable inert solvent contained in a stirred flask, and the chlorination effected by heating, irradiation with light, or catalytically induced such as by stannic chloride or a variety of combinations thereof. Alternatively, methallyl chloride or isocrotyl chloride may be employed as starting materials in place of the isobutylene, or in combination therewith.

The chlorofluorination or fluorination reaction according to the invention is carried out either in fluidized or fixed bed by passing the organic mixture, together with anhydrous HF and chlorine, into a heated tubular reactor packed with the chromium oxide or metal fluoride chlorofluorination catalyst. The reactor is maintained at a temperature of from about 300° to 500° C., with 375° to 450° C. being the preferred. There is a considerable exotherm and the reactor temperature is that which is measured at the hot spot. The contact time desirably ranges from between about 1 and 50 seconds, with 5 to 20 seconds being the preferred range. The chlorine/organic mole ratio is between 1:1 to 20:1, preferably between 3:1 to 7:1. The HF/organic mole ratio is between 2:1 and 20:1, with 4:1 to 10:1 being the preferred range.

One catalyst used in the process according to the invention is chromium oxide, the same being commercially available, for example, from Pfizer Chemical as chipped chromium oxide hydrate. Any off-the-shelf chromium oxide hydrate as received is not in and of itself suitable for use as a chlorofluorination or fluorination catalyst without prior conditioning. Such catalyst is conditioned by heating in the presence of an inert carrier gas for from 24 to 48 hours, as the temperature is raised in stages from about 150° to 400° C. At this point the catalyst bed is cooled to about 200° C. Anhydrous HF is then passed over the chromium oxide for 8 to 16 hours as the temperature is next raised in stages to about 400° C. Other conditioning procedures or conditions are equally well adapted to produce a catalyst suitable for use in the process of the invention. In general, any one of a number of chromium oxide catalysts are suitable for use in the subject process. Examples of such catalysts are set forth in U.S. Pat. Nos. 2,745,867, 3,235,612, 3,258,500 and 3,413,363. Also effective in the process of the invention is a supported chromium oxide catalyst, e.g., chromium oxide coated onto a typical art recognized substrate or support such as carbon, alumina, calcium fluoride, magnesium fluoride, or sodium magnesium fluoride. Similarly, chromium oxide catalyst modified with various metal salts are also within the ambit of this invention; compare, for example, British Patent Specification No. 1,283,386.

The chlorofluorination or fluorination reactions can also be conducted over metal fluoride catalysts such as $AlF_3$, $FeF_3$, $KMgF$, $V_2OF_4$, $ZrF_4$, $CoF_2$, $CrF_3$, and the like. Compare e.g., British Patent Specification No. 823,519 and U.S. Pat. Nos. 2,669,590 and 3,650,987. Preferred are the polyvalent, or transition or Group VIII metal fluorides, and most preferably same are coated onto the art recognized supports, a typical example being the chlorofluorination catalyst prepared by coating $FeF_3$ onto activated carbon.

Useful promoters when utilized in conjunction with the subject chromium oxide catalysts are such materials as $NiO$, $Fe_2O_3$, $ZnO$, $Al_2O_3$, $SrO_2$, $Al_2O_3$-$SrO_2$, $TiO_2$ or $AlF_3$-$Al_2O_3$.

In order to further illustrate the invention and the advantages thereof, the following specific examples are given, it being understood that the same are intended only as illustrative and in nowise limitative.

EXAMPLE I

Commercially available chromium oxide hydrate chipped catalyst (about 275 cc. 4–8 mesh pellets) were charged into a 1 inch I.D. × 27 inches long Inconel reactor (fluorinator) mounted in an electrically heated furnace equipped with means for maintaining in the reactor a temperature between 300° and 500° C. The inlet end of the reactor was connected to a 1 inch I.D. × 14 inches long unpacked Inconel prechlorinator, also electrically heated. The inlet end of the prechlorinator was provided with facilities for metered introduction of vaporous reactants and the outlet end of the fluorinator was connected to the inlet end of a typical product recovery system. For completion of preparation or conditioning of the catalyst prior to use of same, the chromium oxide hydrate pellets in the reactor were heated to 200° and then to 400° C. for about 48 hours or until the heater exit contained no water of dehydration. Thereafter the catalyst was cooled to 200° C. and treated with anhydrous hydrogen fluoride at 200° to 400° C. for about 16 hours.

Subsequent to catalyst conditioning, the temperature in the fluorinator was rasised to 425° c. and was so maintained throughout the run. The temperature in the prechlorinator was maintained at 375° C. during the run. Over a period of 6 hours, about 27 g. (0.48 mols) of isobutylene, 273 g. (3.85 mols) of chlorine, 102 g. (5.10 mols) of anhydrous HF and 42 liters (1.75 mols) of nitrogen diluent were simultaneously metered into the reactor and through the catalyst bed. The isobutylene, $Cl_2$, HF and nitrogen mole ratio was about 1:8:10:1, and the charging of the reactants was such that contact time in the prechlorinator was about 5 seconds and in the fluorinator was about 10 seconds. About 84.5 g. of organic were collected in the water and cold traps. Excess chlorine collected was 39 g. (0.53 mols). The water scrubber liquor was titrated for total acid and HCl and about 9.09 mols acid and 6.44 mols $Cl^-$ were obtained. The organic condensate was analyzed by GLC and 65.26 area percent of $(CF_3)_2C = CHCl$ was determined to be present. The presence of $(CF_3)_2C = CHCl$ was also confirmed as the main component via gas chromatography/mass spectroscopy and NMR ($H_1$, $F^{19}$ and $C^{13}$), as well as by infrared spectrogram. Assuming area percent to be equivalent to weight percent, 55.6 g., (0.278 moles) of $(CF_3)_2C = CHCl$ were formed for a 58 percent yield.

EXAMPLE II

The reaction system used in this example was similar to that of Example I except that the heated prechlorinator (1 inch I.D. × 14 inches long reactor) was not used before the fluorinator, i.e., the reactants were metered directly to an inlet connected to the fluorinator. The temperature in the fluorinator was maintained at 425° C. during the run. Over a period of 6 hours, about 27 g. (0.48 mols) of isobutylene, 272 g. (3.85 mols) of chlorine, 99 g. (4.95 mols) of anhydrous HF and 42 liters (1.75 mols) of nitrogen diluent were simultaneously metered into the reactor and through the catalyst bed. The isobutylene, $Cl_2$, HF and nitrogen mole ratio was about 1:8:10:1 and the contact time was about 10 seconds. About 85 g. of organics were collected in the water and cold traps. Excess chlorine collected was 20.5 g. (0.29 mols). The water scrubber liquor was titrated for total acid and HCl and about 9.68 mole acid and 6.58 mols $Cl^-$ were obtained. The organic condensate was analyzed by GLC and 45.48 area percent of $(CF_3)_2C = CHCl$ was determined to be present. Again assuming area percent to be equivalent to weight percent 38.5 g. (0.193 moles) of $(CF_3)_2C = CHCl$ were formed for a 40.1 percent yield.

EXAMPLE III

The reaction system used in this example was similar to that of Example I. The temperature in the fluorinator was maintained at 425° C. and the temperature in the preheater (prechlorinator) was maintained at 300° C. during the run. Over a period of 3 hours, about 108 g. (0.55 mols) of partially chlorinated isobutane derivatives, 189 g. (2.66 mols) of chlorine, 128 g. (6.40 mols) of anhydrous HF and 13 liters (0.55 mols) of helium diluent were simultaneously metered into the reactor and through the catalyst bed. The organic:$Cl_2$:HF:helium mole ratio was about 1:5:11:1, and the contact time was about 5 seconds. About 85.8 g. of organics were collected in the water and cold traps. Excess chlorine collected was 44 g. (0.62 mols). The water scrubber liquor was titrated for total acid and HCl and about 8.26 mole acid and 5.57 mols $Cl^-$ were obtained. The organic condensate was analyzed by GLC and 64.68 area percent of $(CF_3)_2C = CHCl$ was determined to be present. Again assuming area percent to be equivalent to weight percent, 55.5 g. (0.78 moles) of $(CF_3)_2C = CHCl$ were formed for a 50.5 percent yield.

EXAMPLE IV

Following the procedure of Example III, the temperature in the fluorinator was maintained at 325° C. and the temperature in the preheater was maintained at 300° C. during the run. Over a period of 3 hours, about 62 g. (0.32 mols) of partially chlorinated isobutane derivatives, 110 g. (1.55 mols) of chlorine, 67 g. (3.35 mols) of anhydrous HF and 7.7 liters (0.32 mols) of helium diluent were metered into the reactor and though the catalyst bed. The organic:$Cl_2$:HF:helium mole ratio was about 1:5:10:1 and the contact time was about 10 seconds. About 40.5 g. of organics were collected in the water and the cold traps. Excess chlorine collected was 37 g. (0.52 mols). The water scrubber liquor was titrated for total acid and HCl and about 4.55 mols acid and 2.44 mols $Cl^-$ were obtained. The organic condensate was analyzed by GLC and 13.75 area percent of $(CF_3)_2C = CHCl$ was determined to be present. The yield of $(CF_3)_2C = CHCl$ basis 13.75 area percent reflects that 5.5 g. (0.028 moles) of $(CF_3)_2C = CHCl$ were formed for a 8.72 percent yield.

EXAMPLE V

Following the procedure of Example III, the temperature in the fluorinator was maintained at 425° C. and the temperature in the preheater was maintained at 300° C. during the run. Over a period of six hours, about 353 g. (0.43 moles) of partially chlorinated isobutane derivatives (obtained via the photochlorination of methallyl chloride as per the following Example VII), 382 g. (5.39 moles) of chlorine, 279 g. (13.95 moles) of HF and 33 liters (1.38 moles) of helium diluent were metered into the reactor and through the chomium oxide catalyst bed. The organic: $Cl_2$:HF:helium mole ratio was about 1:4:10:1 and the contact time was 5 seconds. About 272.1 g. of organics were collected in the water and the cold traps. Excess chlorine collected was 151 g. (2.13 moles). The water scrubber liquor was titrated for total acid ahd HCl and about 18.40 moles of acid and 11.85 moles of HCl were obtained. The organic condensate was analyzed by GLC and 56.14 area percent of $(CF_3)_2C = CHCl$ was found. The yield of $(CF_3)_2C = CHCl$ on area percent basis is 154 g. (0.77 moles) or 53.8 percent.

EXAMPLE VI

This example relates to the prechlorination of isobutylene. During a period of 1.75 hours at a temperature of 25° C., a mixture of 11.7 g. (0.21 mole) of isobutylene. 182 g. (2.56 moles) of chlorine and 20.2 liters (0.84 moles) of nitrogen were reacted in an unpacked 1/4 inch I.D. by 16.3 inches long copper tubing. The contact time was 0.23 seconds. The reaction temperature rose to 70° C. in an area about 5 inches from the gas inlet section of the tubing. No heat was applied to the tubing. There were recovered 32 g. of oil in the water scrubber and 140 g. (1.98 moles) of excess chlorine in the caustic scrubber. The chlorine consumed was 0.57 moles. There were recovered 0.42 moles of HCl in the water scrubber. GLC analysis of the recovered oil showed the presence of the following compounds:

| Compound | Area % |
|---|---|
| $(CH_3)_2C = CHCl$ | 1 |
| $(CH_2Cl)_2C(Cl)CH$ | 21 |
| $CHCl_2C(CH_3)ClCH_2Cl$ | 19 |
| $(CH_2Cl)_3CCl$ | 21 |
| $(CHCl_2)_2C(Cl)CH_3$ | 4 |
| $(CH_2Cl)_2C(Cl)CHCl_2$ | 26 |
| $CCl_3C(CH_3)ClCH_2Cl$ | 3 |

The calculated average composition of the oil is $C_4H_{5.8}Cl_{4.2}$.

EXAMPLE VII

This example relates to the photochemical chlorination of methallyl chloride. Into a 5 liter, 3 neck flask equipped with stirrer, reflux condenser, thermometer, gas dispersing tube, were charged 2455 g. (27.2 moles) of methallyl chloride. During a period of 31 hours at a temperature of 25° to 50° C. with the aid of two 275 watt sunlamps, 7125 g. (100.5 moles) of chlorine were charged into the reactor. There were recovered 2514 g. (69.0 moles) of HCl and 918 g. (13.0 moles) of excess chlorine. Chlorine utilization was 87%. The organic mixture recovered, 6427 g., was purged with nitrogen to remove residual HCl and chlorine. GLC analysis of the organic oil showed the following products to be present:

| Compound | Area % |
| --- | --- |
| $(CH_2Cl)_2C(CH_3)Cl$ | 1.56 |
| $(CH_2Cl)_3CCl$ | 0.43 |
| $(CHCl_2)_2C(CH_3)Cl$ | 21.55 |
| $(CH_2Cl)_2C(CHCl_2)Cl$ | 25.25 |
| $CH_3(CCl_3)C(CH_2Cl)Cl$ | 7.09 |
| $(CHCl_2)_2C(CHCl_2)Cl$ | 36.19 |
| $CCl_3(CHCl_2)C(CH_2Cl)Cl$ | 6.93 |
| Others | 1.00 |

The calculated average composition of the oil is $C_4H_{4.5}Cl_{5.5}$.

EXAMPLE VIII

Ferric fluoride on activated carbon catalyst was prepared by heating a mixture of 250 g. "Columbia" CXC activated carbon obtained from Union Carbide Corp. with 60 g. of ferric chloride in 150 g. of water to dryness in a vacuum oven at 100° C. for 24 hours. A 1 I.D. × 27 inches long Inconel reactor, packed with 300 ml of ferric chloride on carbon was heated to 200° C. and gassed with HF to a temperature of 350° C. over a 12 hour period. The ferric chloride was converted to ferric fluoride.

Following the procedure of Example III, the temperature in the ferric fluoride/carbon reactor was maintained at 356° C. and the temperature of the preheater was maintained at 300° C. during the run. Over a period of 6 hours, about 317 g. (1.29 moles) of partially chlorinated isobutane derivatives (obtained via the photochlorination of methallyl chloride as per Example VII), 351 g. (5.85 moles) of chlorine and 251 g. (11.95 moles) of HF were metered into the reactor and through the catalyst bed. The organic:$Cl_2$:HF mole ratio was 1:4.5:9 and the contact time was 5 seconds. About 261 g. of organic product were collected in the water and cold traps. No excess chlorine was collected. The water scrubber liquor was titrated for total acid and HCl and about 18.80 moles of acid and 12.20 moles of HCl were obtained. The organic condensate was analyzed by GLC and 31.10 area percent of $(Cl_3)_2C = CHCl$ was found.

EXAMPLE IX

A chromium oxide on activated carbon catalyst was prepared by heating a mixture of 450 g. $Cr(NO_3)_3 \cdot 9H_2O$ with 284 g. of Union Carbide Corp.'s "Columbia" MBV activated carbon to about 120° C. in a porcelain dish. After all the nitrate had decomposed (as evidenced by the absence of $NO_2$ fumes), the mixture was further dried in vacuum over at 130° C. for 24 hours. About 300 ml of the catalyst were packed into the fluorination reactor and gassed with HF for 7 hours at a temperature of 350° C.

Following the procedure of Example III, the temperature in the chromium oxide/carbon reactor was maintained at 354° C. and the temperature of the preheater was maintained at 300° C. during the run. Over a period of 5 hours, about 251 g. (1.02 moles) of prechlorinated isobutane, 300 g. (4.23 moles) of chlorine and 211 g. (10.05 moles) of HF were passed through the reactor. The organic:$Cl_2$:HF mole ratio was 1:4.23:10 and the contact time was 5 seconds. About 221.8 g. of organic product were recovered from the water and cold trap. Excess chlorine collected was 90 g. (1.26 moles). There were titrated 14.28 moles of acid and 12.60 moles from the water scrubber. The organic condensate was analyzed by GLC and 58.70 area percent of $(CF_3)_2C = CHCl$ was found.

EXAMPLE X

Cobaltous fluoride on activated carbon catalyst was prepared by heating a mixture of 280 g. of Union Carbide (Corp.'s "Columbia" MMV activated carbon with 200 g. of cobaltous chloride in 140 ml of water to dryness in a vacuum oven at 100° C. for 24 hours. About 300 ml of the catalyst was packed into the fluorination reactor and gassed with HF for 7 hours at 360° C. The cobaltous chloride was converted to cobaltous fluoride.

Following the procedure of Example III, the temperature in the fluorinator was maintained at 350° C. and the temperature of the preheater was maintained at 300° C. during the run. Over a period of 5 hours, 273 g. (1.11 moles) of prechlorinated isobutanes, 312 g. (4.39 moles) of chlorine and 221 g. (11.00 moles) of HF were passed through the reactor. The organic:chlorine:HF mole ratio was 1:4:10 and the contact time was 5 seconds. About 210.7 g. of organic product were recovered from the water and cold traps. Excess chlorine recovered were 36 g. (0.50 mole). There were titrated 15.48 moles of acid and 9.46 moles of HCl in the water scrubber. The organic condensate was analyzed by GLC and 49.95 area percent of $(CF_3)_2C = CHCl$ was found.

Thus, the process of this invention provides for the chlorofluorination of isobutylene over certain metal catalysts, i.e., over chromium oxide or metal fluoride chlorofluorination catalysts. Although one and two carbon molecules have been chlorofluorinated over a variety of catalysts, it was unexpected that a $C_4$ compound such as isobutylene could be chlorofluorinated in this manner without massive breakdown and carbonization. The 1-chloro-2-trifluoromethyl-3,3,3-trifluoropropene is moreover produced in high conversion in a continuous flow vapor or liquid phase operation by the process of this invention.

While there have been shown and described and pointed out the fundamental known features of the invention as applied to the preferred embodiment, those skilled in the art will appreciate that various modifications, changes and omissions in the preparation of 1-chloro-2-trifluoromethyl-3,3,3-trifluoropropene from isobutylene illustrated and described can be made without departing from the spirit of the invention. It is the intention, therefore, to be limited only by the scope of the following claims.

What is claimed is:

1. A process for the preparation of 1-chloro-2-trifluoromethyl-3,3,3-trifluoropropene in high yield, comprising prechlorinating an isobutylene feed to such extent that the product of chlorination attains an average chlorine content of at least 4 chlorine atoms per molecule, and thence fluorinating said product of chlorination in a reaction zone by passing said product, together with hydrogen fluoride and chlorine, over a chlorofluorination catalyst selected from the group consisting of a chromium oxide and a metal fluoride chlorofluorination catalyst.

2. The process as defined by claim 1, wherein the prechlorination is effected in a single step.

3. The process as defined by claim 1, wherein the prechlorination is effected in a plurality of steps.

4. The process as defined by claim 1, wherein the chlorine/isobutylene mole ratio in the prechlorination feed ranges from between about 2:1 to 12:1.

5. The process as defined by claim 1, wherein an inert gas stream is utilized to sweep the prechlorination reactants through the prechlorination zone.

6. The process as defined by claim 3, wherein the prechlorination is effected in two prechlorination reaction zones, with the reactant contact time in the first reaction zone ranging from between about 0.01 to 1 second, and the reactant contact time in the second reaction zone ranging from between about 1 and 50 seconds, the temperature in said second reaction zone being maintained at about 300° to 400° C.

7. The process as defined in claim 1, wherein the fluorination reaction zone is maintained at a temperature of from about 300° to 500° C., the reactant contact time in the fluorination reaction zone ranges from between about 1 and 50 seconds, and the hydrogen fluoride/organic mole ratio in said fluorination reaction zone ranges from between 2:1 to 20:1.

8. The process as defined by claim 1, wherein the product of prechlorination comprises a mixture of chloroisobutanes and chloroisobutenes.

9. The process as defined by claim 7, wherein the chlorofluorination catalyst is selected from the group consisting of a polyvalent metal fluoride and a transition metal fluoride.

10. The process as defined by claim 7, wherein the catalyst is chromium oxide.

11. The process as defined by claim 1, wherein the chlorofluorination catalyst is borne by a support selected from the group consisting of carbon, alumina, calcium fluoride, magnesium fluoride and sodium magnesium fluoride.

12. The process as defined by claim 10, wherein the chromium oxide catalyst further includes a metal salt modifier.

13. The process as defined by claim 10, wherein the chromium oxide catalyst further includes a metal oxide promoter, said metal being other than chromium.

14. The process as defined by claim 10, wherein the chromium oxide catalyst is dehydrated chromium oxide hydrate.

15. The process as defined by claim 1, wherein the catalyst is a metal fluoride selected from the group consisting of $AlF_3$, $FeF_3$, $KMgF$, $V_2OF_4$, $ZrF_4$, $COF_2$ and $CrF_3$.

16. The process as defined by claim 13, wherein the promoter is selected from the group consisting of $NiO$, $Fe_2O_3$, $ZnO$, $Al_2O_3$, $SrO_2$, $Al_2O_3$-$SrO_2$, $TiO_2$ and $AlF_3$-$Al_2O_3$.

17. The process as defined by claim 1, wherein the product of prechlorination is condensed and purified prior to passing same over the metal chlorofluorination catalyst.

* * * * *